(12) United States Patent
Yoshida et al.

(10) Patent No.: US 8,026,107 B2
(45) Date of Patent: Sep. 27, 2011

(54) AGGLUTINATION INHIBITION ASSAY METHOD AND REAGENT

(75) Inventors: Tadaaki Yoshida, Ryugasaki (JP); Hiroshi Takahashi, Abiko (JP)

(73) Assignee: Sekisui Medical Co., Ltd., Tokyo (JP)

( * ) Notice: Subject to any disclaimer, the term of this patent is extended or adjusted under 35 U.S.C. 154(b) by 218 days.

(21) Appl. No.: 12/374,726

(22) PCT Filed: Jul. 23, 2007

(86) PCT No.: PCT/JP2007/000785
§ 371 (c)(1), (2), (4) Date: Jan. 22, 2009

(87) PCT Pub. No.: WO2008/012944
PCT Pub. Date: Jan. 31, 2008

(65) Prior Publication Data
US 2009/0263915 A1  Oct. 22, 2009

(30) Foreign Application Priority Data

Jul. 24, 2006 (JP) .................................. 2006-200558

(51) Int. Cl.
*G01N 33/566* (2006.01)
*G01N 33/531* (2006.01)
(52) U.S. Cl. ......... 436/501; 435/7.1; 436/518; 436/523; 436/533; 436/534
(58) Field of Classification Search .................. None
See application file for complete search history.

(56) References Cited

U.S. PATENT DOCUMENTS

| 4,184,849 A | * | 1/1980 | Cambiaso et al. | ............ 436/523 |
| 4,427,781 A | | 1/1984 | Masson et al. | |
| 5,145,784 A | | 9/1992 | Cox et al. | |
| 5,643,732 A | * | 7/1997 | Strahilevitz | .................... 435/7.1 |

FOREIGN PATENT DOCUMENTS

| JP | 57-206859 | 12/1982 |
| JP | 59-173760 | 10/1984 |
| JP | 05-000665 | 1/1993 |
| JP | 2001-337092 | 12/2001 |
| JP | 2004-191332 | 7/2004 |

OTHER PUBLICATIONS

Aoki, K. et al., Forensic Science International, (1996), vol. 77, pp. 151-157.
Extended European Search Report for European Application No. 07790280.7, Oct. 14, 2009.
Kimiko Aoki, "Ran'yo Yakubutsu no Men'eki Sokuteiho," Japanese Journal of Forensic Toxicology, vol. 14, No. 2, pp. 114-117, 1996.

* cited by examiner

*Primary Examiner* — Shafiqul Haq
*Assistant Examiner* — Galina Yakovleva
(74) *Attorney, Agent, or Firm* — Greenblum & Bernstein, PLC

(57) ABSTRACT

Provided are an agglutination-inhibition assay and a reagent for agglutination-inhibition assay, which can be used for measuring a ligand in a sample at high sensitivity in a wide range from the low-concentration range to the high-concentration range and have good reproducibility of measurement. Specifically, provided are an agglutination-inhibition assay and a reagent for agglutination-inhibition assay, in which used are an insoluble carrier particle carrying a ligand, a specific receptor in the free-form and an insoluble carrier particle carrying a specific receptor which binds to a different site on the ligand than the receptor in the free-form.

20 Claims, 1 Drawing Sheet

AGGLUTINATION INHIBITION ASSAY METHOD AND REAGENT

TECHNICAL FIELD

The present invention relates to a method of measuring a ligand in a sample employing an agglutination inhibition reaction of (carrier) particles and to a reagent for the method. In particular, the present invention relates to an agglutination-inhibition assay in which formation of aggregate of, an insoluble carrier particle on which a ligand has been pre-loaded, a free-form receptor which is specific to the ligand, and an insoluble carrier particle carrying the receptor specific to the ligand, is inhibited by a ligand in the sample and to a reagent for agglutination-inhibition assay.

BACKGROUND ART

Methods of measuring a ligand qualitatively and quantitatively by causing or inhibiting agglutination of particles using insoluble carrier particles are performed easily at high sensitivity. Therefore, various measurement reagents have been developed using ligand-receptor reaction principles such as immunoreactions between antigens and antibodies or binding reactions between complementary nucleic acid chains.

The agglutination method is a method of measuring the degree of agglutination of receptor-sensitized carrier particles due to a crosslinking reaction via ligands to be measured, and the method has been in practical use for many measurement items because of the background of the need for sensitive measurement of trace substances.

On the other hand, the agglutination inhibition method is a method of measuring the ratio of agglutination inhibition, by a ligand to be measured, between ligand- or ligand-like substance-sensitized carrier particles and a receptor. In the case of the agglutination method, multiple kinds of specific receptors are required except for unusual kinds of ligands, while in the case of the agglutination inhibition method, a measurement system can be constructed using only one kind of a specific receptor.

Moreover, as for the immunoreactions, the agglutination inhibition method is advantageous, for it does not cause hook effect (superficial reduction of reaction, a phenomenon caused by excessive antigen). However, the method has been employed, in most of the cases so far, for a low-molecular-weight ligand, such as hapten, which multiple kinds of receptors cannot be used for.

Application of the agglutination inhibition method has been limited because controlling the range of measurement concentration is difficult compared with the agglutination method. In the agglutination method, agglutination progresses in proportion to the amount of the ligand, and hence, the range of measurement can be easily expanded only by enhancing the increase of sensitivity at the high-concentration range as shown in, for example, Patent Document 1 which is related to a latex-enhanced immuno-agglutination method.

On the other hand, as for the range of measurement of the agglutination inhibition method where the agglutination inhibition reaction progresses in proportion to the amount of ligand, the upper limit of measurement at a high-concentration range of the ligand basically depends on the degree of the initial agglutination (agglutination in the absence of the ligand), while the lower limit of measurement at a low-concentration range of the ligand depends on the sensitivity of the agglutination inhibition reaction. Therefore, it is necessary to consider both factors together.

Patent Document 2 discloses a method using a non-specific agglutination-promoting substance in measurement of hapten, as a method for enhancing the initial agglutination in the agglutination inhibition method. This method can measure a ligand at a high-concentration range and extend the upper limit of measurement, but the sensibility to the agglutination inhibition reaction is lowered because of enhancement of agglutination which is irrelevant to a specific reaction between the ligand and receptor, resulting in significant deterioration of detectability at a low-concentration range.

Meanwhile, Patent Document 3 discloses an agglutination inhibition method using a carrier sensitized with a single monoclonal antibody and a carrier sensitized with an antigen. In this method, the detectability at the low-concentration range is improved without impairing the sensibility to the agglutination inhibition reaction, by using a carrier particle which carries a ligand and a carrier particle which carries a receptor, respectively, and by optically enhancing the degree of sensitivity changes. However, in this method, the reaction itself between the antigen and the antibody is not enhanced, and hence the effect of expanding the range of measurement cannot be achieved. Also in the agglutination inhibition method proposed in Patent Document 4, where antigen-sensitizing latex, an antibody, and a receptor specific to the antibody are used, the agglutination is enhanced only by specific reactions between the antigen and the antibody and between the antibody and the receptor, and hence, expansion of the range of measurement, relative to the conventional methods, can be achieved. Protein A used in the example as a receptor, however, has reactivity to any antibodies (IgG), and hence, this method is not suitable for measurement of serum or plasma samples containing the IgG In addition, the anti-mouse IgG rat monoclonal antibody is not a commonly used material and may be difficult to obtain. Moreover, the measurement principle itself is through the biphasic reaction of the antigen-antibody and the antigen-receptor, and the performance may be lowered depending on the measurement device and the method.

As described above, neither an agglutination-inhibition assay nor a reagent for agglutination-inhibition assay, which have opposing properties of strong initial agglutination and high sensitivity to the agglutination inhibition reaction, has been established, and it has been difficult to measure, with high reproducibility, normal ligands, for example, ligands having multiple receptor binding sites, at high sensitivity in a wide range by conventional assays.

Patent Document 1: JP 2004-191332 A
Patent Document 2: JP 05-000665 B
Patent Document 3: JP 59-173760 A
Patent Document 4: JP 2001-337092 A

DISCLOSURE OF THE INVENTION

Problem to be Solved by the Invention

The present invention is a solution for the above-mentioned problems of the conventional art, and the object of the present invention is to provide an agglutination-inhibition assay and an assay reagent thereof, which can measure a ligand in a sample at high sensitivity in a wide range, from a low-concentration range to a high-concentration range, and with good reproducibility.

Means for Solving the Problem

The inventors of the present invention have made extensive studies on an agglutination-inhibition assay. Consequently, the inventors have found out that the use of an insoluble carrier particle with a ligand, a specific receptor in the free-form, and an insoluble carrier particle with a specific receptor which binds to a different site on the ligand than the free-form receptor, can enhance initial agglutination while maintaining the sensitivity to an agglutination inhibition reaction, can measure the ligand at very high sensitivity in a wide range from a low-concentration range to a high-concentration range, and can achieve good reproducibility of measurement, thus completing the present invention.

That is, the present invention includes the following constitution.

(1) A method for measurement of agglutination inhibition comprising, mixing a sample containing a ligand to be measured having multiple receptor-binding sites with the following (A) to (C):

(A) an insoluble carrier particle which preliminarily carries a ligand or a ligand-like substance, (B) a free-form receptor which reacts specifically with the ligand, and (C) an insoluble carrier particle which reacts specifically with the ligand and carries a receptor which binds to a different site on the ligand than the free-form receptor; and measuring an agglutination inhibition reaction of the particles responsive to an amount of the ligand to be measured in the sample.

(2) A method for measurement of agglutination inhibition according to the item (1), in which the insoluble carrier particle is a latex particle.

(3) A method for measurement of agglutination inhibition according to the item (1) or (2), in which the receptor is an antibody or a fragment including a functional site thereof, the ligand is an antigen, and the agglutination inhibition reaction of the particles is measured based on immunoreactions between the receptor and the ligand.

(4) A method for measurement of agglutination inhibition according to any one of the items (1) to (3), in which both the free-form receptor and the receptor carried on the insoluble carrier particle are monoclonal antibodies.

(5) A method for measurement of agglutination inhibition according to any one of the items (1) to (4), in which the ligand to be measured is human albumin, and the receptor is an anti-human albumin monoclonal antibody.

(6) A method for measurement of agglutination inhibition according to any one of the items (1) to (5), in which an average particle diameter of the insoluble carrier particle which carries the receptor is one half ($1/2$) to one tenth ($1/10$) an average particle diameter of the insoluble carrier particle which carries the ligand or ligand-like substance.

(7) A reagent for agglutination-inhibition assay comprising the following (A) to (C):

(A) an insoluble carrier particle which carries a ligand or a ligand-like substance, (B) a free-form receptor which reacts specifically with the ligand, and (C) an insoluble carrier particle which reacts specifically with the ligand and carries a receptor which binds to a different site on the ligand than the free-form receptor, the assay being for measurement of an agglutination inhibition reaction of particles responsive to an amount of ligand to be measured in a sample.

(8) A reagent for agglutination-inhibition assay according to the item (7), in which the insoluble carrier particle is a latex particle.

(9) A reagent for agglutination-inhibition assay according to the item (7) or (8), in which the receptor is an antibody or a fragment including a functional site thereof, and the ligand is an antigen, the assay reagent being for measuring the agglutination inhibition reaction of the particles based on immunoreactions between the receptor and the ligand.

(10) A reagent for agglutination-inhibition assay according to any one of the items (7) to (9), in which both the free-form receptor and the receptor which binds to a different site on the ligand than the free-form receptor are monoclonal antibodies.

(11) A reagent for agglutination-inhibition assay according to any one the items (7) to (10), in which the average particle diameter of the insoluble carrier particle which carries the receptor is one half ($1/2$) to one tenth ($1/10$) the average particle diameter of the insoluble carrier particle which carries the ligand or ligand-like substance.

(12) A reagent for agglutination-inhibition assay according to any one of the items (7) to (11), in which the ligand to be measured is human albumin, and the receptor is an anti-human albumin monoclonal antibody.

Effects of the Invention

The agglutination-inhibition assay and reagent for agglutination-inhibition assay of the present invention can measure a ligand to be measured at high sensitivity in a wide range from a low-concentration range to a high-concentration range and have good reproducibility of measurement. In particular, in the case where the assay is performed by using an immunoreaction, the assay has a characteristic that no hook effect occurs, and hence measurement of a ligand which may show an abnormally high level can be performed at higher reliability than the particle agglutination method. In addition, in the case where a monoclonal antibody is used as a receptor of the present invention, ligand fragments might be measured, as the agglutination inhibition reaction occurs as long as the ligand fragments include an epitope. Therefore, the assay can measure the fragmented ligand in the same way as in the case of a full-length ligand.

BEST MODE FOR CARRYING OUT THE INVENTION

Samples to be Measured

Examples of the sample containing a ligand to be measured in the present invention include human or animal blood, serum, plasma, culture supernatant, urine, spinal fluid, saliva, sweat, ascites fluid, or cell or tissue extract.

(Ligands)

The ligand to be measured in the present invention may include any substance as long as the ligand is a substance having multiple receptor binding sites. Specifically, examples thereof include proteins such as C-reactive protein (CRP), FDP, D-dimer, prostate-specific antigen (PSA), hemoglobin A1c, albumin, pepsinogen I (PGI), pepsinogen II (PGII), matrix metalloproteinase (MMP), trypsin, chymotrypsin, elastase, and cathepsin, and in addition, peptides, sugars, nucleic acids, lipids, and polymer agents. In theory, all of the ligands (if the ligands are antigens, ligands having multiple epitopes (antigenic determinants), for example, ligands that can be detected by a sandwich assay using two kinds or more monoclonal antibodies) having multiple receptor binding sites may be used as substances to be measured. The ligand-like substance is one which has the same or similar reactivity (antigenicity if the ligand is an antigen) as that of the above-mentioned ligands in terms of the relationship with receptors. Examples of the ligand-like substance include: a fragment that may be obtained by decomposition of ligands (such as antigens), a recombinant ligand that may be obtained by genetic engineering, and a substance that has similar ligand structures (ligand analogs).

(Receptors)

The receptor to be used in the present invention is a substance which binds specifically to a ligand to be measured. Generally, an anti-ligand polyclonal antibody or anti-ligand monoclonal antibody obtained by immunizing a rabbit, sheep, goat or the like, with a ligand to be measured, may be used. Of those, the monoclonal antibody is particularly desirably used from the viewpoint of specificity. The antibody to be used may be an antibody fragment prepared in accordance with a conventional method. In addition, for some kinds of ligands, lectins, nucleobases, or the like may also be used as a receptor singly or in combination with an antibody.

The kind of the receptor used in the present invention is not particularly limited as long as multiple kinds of receptors are used, and a free-form receptor should be different from a receptor immobilized on a carrier. That is, the free-form receptor and the receptor immobilized on a carrier should bind to different sites on the ligand. That is, the receptors may be ones which do not interfere mutually with bindings to the ligand. Moreover, both of the free-form receptor and the receptor immobilized on a carrier are desirably monoclonal antibodies. In the present invention, by using both of the free-form receptor and the receptor immobilized on a carrier in combination, it is possible to promote initial agglutination and to increase a sensitivity change in a high-concentration range, resulting in expanding the measurable range. The type, the content, and the form of existence (free-form or carrier-immobilized form) of the receptor may be appropriately selected considering the number of receptor binding sites on the ligand, the degree of agglutination of a particle necessary for analysis, and the target range of measurement.

In the case where monoclonal antibodies are used as the receptors, the antibodies may be selected by, for example, the following procedures.

First, the reactivity between a ligand to be measured and a monoclonal antibody prepared using the ligand as an immunogen is confirmed by Western blotting or ELISA to select multiple kinds of antibodies showing high reactivity. Then, the reactivity of the selected antibodies when used in combination is confirmed by a sandwich ELISA. Desirably, the combination of the monoclonal antibodies should be appropriately selected depending on the object of measurement and the required performance because the higher the reactivity, the higher the sensitivity and the possibility of expanding the range of measurement. The resultant combination of monoclonal antibodies would be employed in an actual measurement system in a state where one monoclonal antibody be immobilized on a carrier, while the other be in a free-form without being immobilized on a carrier, then an optimal combination would be finally determined considering the initial agglutination, the measurement sensitivity, the range of measurement, the cross-reactivity with substances which are not the object of measurement and have similar structures to the ligand.

(Carrier Particles)

The insoluble carrier particles to be used for carrying a ligand or a receptor in the present invention are not particularly limited, and latex with an average particle diameter of 50 to 1,000 nm is preferable. The material of the latex may be a material suitable for carrying a ligand or a receptor. In addition to generally used latex mainly formed of polystyrene, the example includes: a styrene-butadiene copolymer, polymers of (meta)acrylate esters polymers, and the like. In addition, particles each formed of material such as metal colloids, gelatin, liposomes, microcapsules, silica, alumina, carbon black, metal compounds, metal, ceramics, or magnetic substances may be used. As a method of allowing carrier particles to carry the ligand, or the ligand-like substance, and the receptor, chemical bonding methods as well as generally used physical adsorption methods may be employed.

The carrier particles that carry the ligand and the carrier particles that carry the receptor to be used in the present invention may be made of the same material or different materials. Diameters of the respective carrier particles may be selected so that the diameters are suitable for the purpose or the analysis method. However, in order to sufficiently achieve the effect of the present invention, the average particle diameter of a carrier particle that carries the receptor is preferably one half ($\frac{1}{2}$) to one tenth ($\frac{1}{10}$) the average particle diameter of the carrier particle which carries the ligand.

(Buffers)

The agglutination reaction in the present invention is performed in a buffer, and the type, concentration, and pH of the buffer are selected so that the agglutination reaction can be performed in an optimal manner. Examples of the buffer to be used include a phosphate buffer, a Tris-HCl buffer, a carbonate buffer, a glycine buffer, and a Good's buffer. The concentration of a buffering agent in the buffer is about 5 mM to 500 mM, and the pH is in the neutral to basic range in many cases (usually, in the range of 7.0 to 9.5).

(Measurement Method of Signal of Agglutination)

The method of measuring the signals of agglutination may be any method as long as the method is usually used for measurement of an agglutination inhibition reaction. Examples of the method include techniques employed by those skilled in the art such as: evaluation based on absorbance ratios; count of particles; measurement of particle sizes (the sizes become larger if agglutination occurs); measurement of scattered light; and measurement of absorption spectra (the spectra are increased or shifted if agglutination occurs). Moreover, it is also feasible to employ an electrochemical detection method instead of the optical detection method, if possible.

As described above, there are various methods of measuring the signal of agglutination, but a method using latex particles and a general-purpose biochemical analyzer is convenient. For example, the method is performed by: adding a reagent which contains latex (carrying a receptor of a type different from the free-form receptor) and an insoluble carrier particle (such as latex carrying a ligand), to a sample containing a ligand to be measured; heating the mixture at a certain temperature for a certain period of time; measuring absorbance during such period to detect changes in the absorbance; and calculating the concentration of the ligand in the test sample based on a calibration curve created for a standard solution having a known concentration as a sample. In a usual latex agglutination inhibition method, absorbance is measured at wavelengths of 500 to 900 nm, and quantification is generally performed based on the changes in the absorbance during the reaction. The range of measurement in the present invention can be appropriately set in a desired range of the measurement considering the type of the ligand to be measured, the avidity of the receptor, and the ratio of the amount of the receptors. For example, in the case where the object of measurement is urinary albumin, the range is preferably 1 μg/mL to 1 mg/mL in view of use in clinical tests. As shown in Example below, the albumin can be measured accurately by the present invention.

The reagent for agglutination-inhibition assay of the present invention includes: (A) an insoluble carrier particle on which a ligand or a ligand-like substance is preloaded, (B)

a free-form receptor which reacts specifically with the ligand, and (C) an insoluble carrier particle which carries a receptor that reacts specifically with the ligand and binds to a site different from where the free-form receptor does so on the ligand, and it is desirable to divide the reagent into the first reagent including (B) and (C) and the second reagent including (A).

Hereinafter, the present invention will be described in more detail by way of examples, but the present invention is not limited thereto.

EXAMPLES

Measurement of Trace Amount of Albumin by Agglutination-Inhibition Assay (1) Preparation of Receptor (Anti-Albumin Monoclonal Antibody)

One hundred (100) μg of purified human albumin (manufactured by Sigma-Aldrich Corporation) was used per one immunization. The first immunization was performed by injecting 200 μL of emulsion, prepared by mixing albumin and Freund's complete adjuvant in an equal amount, to the peritoneal cavity of each BALB/c mouse. The booster was performed by repeating the intraperitoneal injection three times at the intervals of two weeks with 200 μL of emulsion, prepared using Freund's incomplete adjuvant in the same way as above.

The antibody titer in blood collected from the eyeground vein of each mouse was measured by ELISA using purified human albumin in the solid phase, and mice having high antibody titer were selected and used for cell fusion (the method of confirming the antibody titer was the same as the following method of confirming the presence of an anti-albumin antibody in a culture supernatant). Two weeks after the fourth immunization, a solution obtained by dissolving 100 μg of albumin in 200 μL of physiological saline was injected to the murine peritoneal cavity, and three days later, the spleen were extirpated. The extirpated spleen was gently crushed in an RPMI 1640 medium, and the suspension was centrifuged at 1,500 rpm to recover spleen cells. The resultant cells were washed with an RPMI 1640 medium devoid of fetal bovine serum, by repeating centrifugation and precipitation three times or more, and the precipitate was suspended in 2 mL of an RPMI 1640 medium containing 15% fetal bovine serum, to thereby prepare a spleen cell suspension. The spleen cells and myeloma cells SP2/O-AG14 were mixed at a ratio of six to one (6:1) in terms of the number of the cells, and the cells were allowed to fuse in the presence of 50% polyethylene glycol. The precipitates were collected by performing centrifugation at 1,500 rpm, then suspended and centrifuged in a GKN solution (prepared by dissolving 2 g of glucose, 0.4 g of potassium chloride, 8 g of sodium chloride, 1.41 g of disodium hydrogen phosphate, and 0.78 g of disodium hydrogen phosphate dihydrate in purified water to give 1 liter) to wash the cells, followed by recovery of the precipitates. A suspension obtained by suspending the resultant precipitates in 30 mL of an RPMI 1640 medium containing 15% fetal bovine serum was pipetted in an amount of 100 μL per well, and an HAT medium containing $2.5 \times 10^6$ thymocytes of a BALB/c mouse as feeder cells was pipetted into the same well in an amount of 200 μL per well. The suspensions were pipetted to three 96-well microplates, and the cells were cultured at 37° C. in a 5% carbon dioxide gas incubator.

The presence of the anti-albumin antibody in the culture supernatant was confirmed by ELISA using purified human albumin immobilized on the solid phase. Ten days after culture, proliferation of the fused cells was confirmed in all the wells. Details of the method of confirming the presence of the anti-albumin antibody are as follows.

First, 100 μL of 10 mM phosphate buffer (pH 7.2; hereinafter, abbreviated as PBS) containing 10 μg/mL albumin and 150 mM sodium chloride was pipetted into 96-well microplates, and the plates were allowed to stand at 4° C. overnight. Next, the plates were washed three times with 300 μL of PBS containing 0.05% Tween 20 and 1% bovine serum albumin, and the culture supernatants of the respective wells in the three 96-well microplates used for each culture were added thereto at 50 μl/well. The plates were allowed to stand at room temperature for 1 hour. Thereafter, the plates were washed three times with PBS containing 0.05% Tween 20, then the peroxidase-labeled anti-mouse antibody (Daiichi Pure Chemicals Co., Ltd.) was added at 50 μL/well. The plates were allowed to stand at room temperature for 1 hour. The plates were washed three times with PBS containing 0.5% Tween 20, then a citrate buffer (pH 5) containing 0.2% ortho-phenylenediamine and 0.02% hydrogen peroxide was added at 50 μL/well. The plates were allowed to stand at room temperature for 15 minutes, and 4.5 N sulfuric acid was added at 50 μL/well to stop the reaction, followed by measurement of absorbance at a wavelength of 492 nm. Based on the result of the measurement, the wells with high absorbance were selected as the wells in which the anti-albumin antibodies were present (that is, anti-albumin antibody-producing fused cells were present) (positive wells).

Monoclonal selection was performed by the limiting dilution method. That is, BALB/c mouse thymocytes were pipetted as feeder cells into 96-well microplates at $10^6$ cells/well, and a suspension, obtained by diluting the fused cells from the positive wells to 10 cells/mL, was pipetted thereinto at 0.1 mL/well. Culture was performed in 5%-carbon dioxide incubator at 37° C. for 10 days using an HT medium for the initial culture and an RPMI 1640 medium containing 15% fetal bovine serum for the cultures thereafter. The above-mentioned selection of positive wells by ELISA using purified human albumin immobilized on the solid phase and the above monocloning procedures by the limiting dilution method were repeated three times, to thereby obtain 30 kinds of anti-albumin monoclonal antibody-producing cells. About $10^5$ cells for each kind were administered intraperitoneally to pristane-treated mice, and the ascites of the mice were separately collected. The resultant ascites were each centrifuged to remove insoluble matters, and an equal amount of saturated ammonium sulfate solution was added. The resultant solutions were allowed to stand under stirring overnight, and the precipitates were recovered by centrifugation. The recovered precipitates were dissolved in a 20 mM Tris buffer (pH 8) and dialyzed against the buffer. The each dialyzed solution was equilibrated with the buffer and separately adsorbed on DEAE-Sepharose columns, and elution was performed with a sodium chloride-concentration gradient of from 0 to 300 mM in the same buffer. The resultant IgG fractions were dialyzed against 50 mM glycine buffer to obtain 30 kinds of purified antibodies, and a combination of two kinds of the antibodies, which provides the highest sensitivity in the sandwich method (antibody 1-8 and antibody 3-8), was selected from the resultant antibodies.

(2) Preparation of Latex Reagent for Measurement of Albumin

To 3 mL of 20 mM Tris buffer (pH 8.5) containing antibody 3-8 (2.8 mg/mL) selected from the above-mentioned two kinds of anti-albumin monoclonal antibodies, was added 3 mL of a suspension of 4% latex with an average particle diameter of 50 nm (manufactured by Sekisui Chemical Co., Ltd.), then the whole was stirred at 4° C. for 2 hours. 6 mL of a 20 mM Tris buffer (pH 8.5) containing 0.4% bovine serum albumin were added to the suspension, and the whole was stirred at 4° C. for 1 hour. The resultant was centrifuged, and the precipitates were resuspended in a 5 mM MOPS buffer (pH 7.0) so that the absorbance of the suspension was 40 mOD at a wavelength of 600 nm, to thereby prepare anti-albumin antibody 3-8-sensitizing latex. The free-form antibody 1-8 and antibody 3-8-sensitizing latex were mixed to prepare the first reagent.

Next, 3 mL of a suspension of 0.5% latex with an average particle diameter of 300 nm (manufactured by Sekisui Chemical Co., Ltd.) was added to 3 mL of 10 mM CHES buffer (pH 5.5) containing 0.5 mg/mL human serum albumin, and the whole was stirred at 4° C. for 1 hour. The resultant was centrifuged, and the supernatant was removed. The precipitates were resuspended in a 5 mM MOPS buffer (pH 7.0) so that the absorbance of the suspension was 2.15 OD at a wavelength of 600 nm, to thereby prepare the second reagent as an albumin-sensitizing latex solution.

(3) Measurement of Albumin

Measurement was performed for albumin samples with different concentrations using a general-purpose autoanalyzer, HITACHI 7170, to confirm measurement sensitivity. Specifically, 3 μL each of sample solutions containing different concentrations of albumin were added to 100 μL aliquats of the first reagent and the whole was stirred and warmed at 37° C. for 5 minutes. Then, 100 μL of the second reagent was added thereto, and absorbance changes at 37° C. for 5 minutes at a main wavelength of 570 nm and a sub-wavelength of 800 nm were measured. First, Table 1 shows the initial agglutination at an albumin concentration of 0 μg/mL. Moreover, an absorbance change after the initial agglutination in the case of the measurement of each sample containing 5, 12.5, 25, 50, 100, 200, 400, and 800 μg/mL albumin, respectively, was measured, and the results are shown in FIG. 1 by a solid line as a reaction curve of the albumin concentration versus–(minus) absorbance (hereinafter, shown in the same way). Based on the shape of the reaction curve, a calibration curve was created with six points of 0, 5, 25, 100, 400, and 800 μg/mL. The absorbance changes in the albumin samples containing different concentrations of albumin were converted into albumin concentrations, and the measurements were shown in Table 2.

(4) Comparative Examples

The following five kinds of the first reagents (A) to (E) were prepared as Comparative Examples so that the final antibody concentrations were the same as Example.
(A) The first reagent containing the free-form antibody 1-8 only
(B) The first reagent containing the antibody 1-8-sensitizing latex only
(C) The first reagent containing both the free-form antibody 1-8 and the antibody 1-8-sensitizing latex
(D) The first reagent containing both the free-form antibody 1-8 and the free-form antibody 3-8
(E) The first reagent containing both the antibody 1-8-sensitizing latex and the antibody 3-8-sensitizing latex Each of the first reagents (A) to (E) was combined with the second reagent prepared in (2), and measurement was performed in accordance with the method described in (3). In the same way as in Example, Table 1 shows the results of the initial agglutination, FIG. 1 shows the reaction curves of the albumin concentration versus–absorbance, and Table 2 shows the measurements obtained by: creating a calibration curve from optimal concentration points selected from the range of 0 to 800 μg/mL based on the shapes of the reaction curves of Comparative Examples; and converting absorbance changes, in the samples containing different concentrations of albumin, into albumin concentrations.

(5) Results

As shown in Table 1, the initial agglutination (absorbance) of Comparative Examples A, B, and C and that of Comparative Example D were found to be about half and about two third (⅔) the initial agglutination of Example, respectively. Therefore, it was easily estimated that the reagents of the Comparative Examples are inferior in basic measurement performance in the agglutination inhibition method. On the other hand, the initial agglutination of Comparative Example E was found to be larger than that of Example.

TABLE 1

| Example |   | 332.3 |
|---|---|---|
| Comparative | A | 157.3 |
| Example | B | 185.2 |
|  | C | 144.4 |
|  | D | 214.3 |
|  | E | 438.3 |

Unit (mA b s)

The reaction curve of the albumin concentration versus–(minus) absorbance shown in FIG. 1 revealed that, the reagent of Example (-●-) had high sensibility to the agglutination inhibition reaction and showed large sensitivity (-absorbance) changes within the albumin low-concentration range (5-50 μg/mL) and clear sensitivity changes also within the albumin high-concentration range (100-800 μg/mL), and hence it was confirmed that the reagent was able to measure albumin at high accuracy within wide ranges from the low-concentration range to the high-concentration range. On the other hand, the reagents of Comparative Examples A (-□-) and C (-Δ-) show little sensitivity change in the low-concentration range of albumin, and hence the reagents cannot measure albumin accurately in the low-concentration range. Meanwhile, in the case of Comparative Example D (-x-), whereas the shape of the reaction curve of the albumin concentration versus–absorbance is similar to that of Example, the initial agglutination and sensitivity changes are smaller than those of Example, leaving the problem of poor measurement accuracy. The reagents of Comparative Examples B (-○-) and E (---) show large sensitivity changes within the albumin low-concentration range but no change in the high-concentration range, and hence the reagents cannot measure albumin in wide ranges from the low-concentration range to the high-concentration range.

As shown in Table 2, in Example, the measurements for albumin from the low concentration to the high concentration were found to be almost the same as theoretical values. In Comparative Examples A and C, it was impossible to measure albumin accurately at the low-concentration range including 0 μg/mL albumin. Meanwhile, in Comparative Examples B and E, it was impossible to measure albumin at the high-concentration range. In Comparative Example D, the measurements in general were far from the theoretical values in any concentration areas and found not to be accurate.

TABLE 2

| Albumin concentration | Example | Comparative Example A | Comparative Example B | Comparative Example C | Comparative Example D | Comparative Example E |
|---|---|---|---|---|---|---|
| 0 | 0.0 | 6.9 | 0.0 | 2.5 | 0.0 | 0.0 |
| 5 | 4.2 | 0.0 | 5.8 | 7.2 | 4.2 | 5.2 |
| 12.5 | 12.1 | 0.0 | 11.9 | 19.0 | 7.0 | 11.9 |
| 25 | 26.9 | 17.9 | 24.4 | 26.1 | 18.2 | 25.7 |
| 50 | 50.1 | 34.0 | 50.2 | 58.4 | 45.2 | 49.4 |
| 100 | 97.7 | 100.4 | 103.5 | 111.8 | 88.8 | 64.1 |
| 200 | 206.6 | 194.0 | 134.6 | 178.5 | 198.6 | 68.0 |
| 400 | 405.7 | 398.8 | 153.0 | 418.3 | 330.0 | 69.7 |
| 800 | 809.0 | 808.3 | 155.3 | 785.4 | 684.0 | 70.4 |

Unit (μg/ml)

For the above-mentioned Example and Comparative Examples, simultaneous reproducibility tests were performed under the same conditions (n=5). Table 3 shows the results.

As shown in Table 3, in Example, the measurements for albumin showed high reproducibility, from the low concentration to the high concentration, and provided variation coefficients of 6% or less, and the average measurements were almost the same as the levels of albumin concentration. In the cases of Comparative Examples A, C, and D, the reproducibility was low, and in particular, the variation coefficients at the low concentrations were sometimes more than 20%. In the cases of Comparative Examples B and E, measurement was performed at high reproducibility, but the average measurements at the high-concentration range were far from the levels of albumin concentration, and hence, the accuracy was low.

TABLE 3

| Albumin concentration | Reproducibility (n = 5) | Example | Comparative Example A | Comparative Example B | Comparative Example C | Comparative Example D | Comparative Example E |
|---|---|---|---|---|---|---|---|
| Level of 12.5 | Average (μg/mL) | 10.8 | 30.4 | 11.4 | 22.5 | 9.7 | 10.9 |
| | Variation coefficient (%) | 5.2 | 47.8 | 4.4 | 24.2 | 15.7 | 4.2 |
| Level of 25 | Average (μg/mL) | 25.5 | 39.9 | 24.8 | 27.4 | 22.7 | 25.9 |
| | Variation coefficient (%) | 3.2 | 33.4 | 1.2 | 24.9 | 8.3 | 1.5 |
| Level of 50 | Average (μg/mL) | 57.3 | 56.1 | 52.8 | 45.3 | 51.8 | 49.9 |
| | Variation coefficient (%) | 3.7 | 15.1 | 7.2 | 20.3 | 5.1 | 0.4 |
| Level of 200 | Average (μg/mL) | 208.6 | 229.0 | 119.8 | 230.7 | 221.8 | 63.6 |
| | Variation coefficient (%) | 1.7 | 3.6 | 2.6 | 3.1 | 2.4 | 0.2 |
| Level of 800 | Average (μg/mL) | 815.7 | 821.2 | 134.6 | 818.7 | 471.2 | 65.1 |
| | Variation coefficient (%) | 0.5 | 0.7 | 3.1 | 1.5 | 2.8 | 0.1 |

Industrial Applicability

According to the present invention, it shall be able to provide an agglutination-inhibition assay and a reagent for agglutination-inhibition assay, which can be used for measuring a ligand at high sensitivity in a wide range from a low-concentration range to a high-concentration range and have good reproducibility of measurement. In particular, in the case where the assay is performed by using an immunoreaction, measurements are highly reliable because the assay has a characteristic that no hook effect occurs. Meanwhile, in the case of measuring a ligand which may show an abnormally high level, the present invention can provide a more accurate measurement method than the particle agglutination method.

Figure 1:
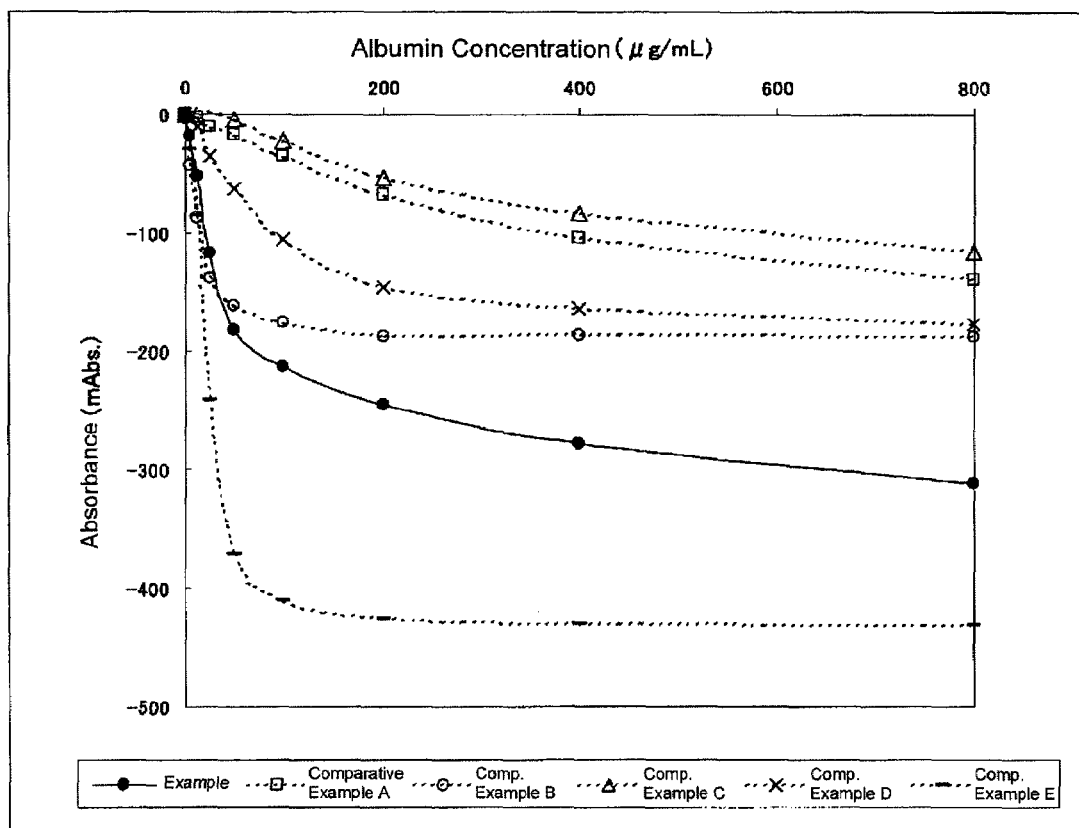
FIG. 1 shows reaction curves of the albumin concentration versus–absorbance in Example and Comparative Examples.

The invention claimed is:

1. A method for measurement of agglutination inhibition comprising,
    mixing a sample containing a ligand to be measured, having multiple receptor binding sites, with the following:
    a first insoluble carrier particle that preliminarily carries a plurality of the ligand or a plurality of a ligand-like substance,
    a first free-form receptor that binds specifically to a site on the ligand or the ligand-like substance, and
    a second insoluble carrier particle that carries a second receptor that is different from the first free-form receptor and binds specifically to a different site on the ligand or the ligand-like substance than the first free-form receptor; and
    measuring an agglutination inhibition reaction of the particles responsive to an amount of the ligand to be measured in the sample.

2. The method for measurement of agglutination inhibition according to claim 1, wherein the first or second insoluble carrier particle is a latex particle.

3. The method for measurement of agglutination inhibition according to claim 1, wherein the receptor is an antibody or a fragment including a functional site thereof, the ligand is an antigen, and the agglutination inhibition reaction of the particles is measured based on immunoreactions between the receptor and the ligand.

4. The method for measurement of agglutination inhibition according to claim 1, wherein both the free-form receptor and the receptor, carried on the second insoluble carrier particle are monoclonal antibodies.

5. The method for measurement of agglutination inhibition according to claim 1, wherein the ligand to be measured is human albumin, and the receptor is an anti-human albumin monoclonal antibody.

6. The method for measurement of agglutination inhibition according to claim 1, wherein an average particle diameter of the second insoluble carrier particle, which carries the receptor is one half (½) to one tenth (¹⁄₁₀) an average particle diameter of the first insoluble carrier particle, which carries the ligand or ligand-like substance.

7. The method for measurement of agglutination inhibition according to claim 2, wherein the receptor is an antibody or a fragment including a functional site thereof, the ligand is an antigen, and the agglutination inhibition reaction of the particles is measured based on immunoreactions between the receptor and the ligand.

8. The method for measurement of agglutination inhibition according to claim 2, wherein both the free-form receptor and the receptor carried on the insoluble carrier particle are monoclonal antibodies.

9. The method for measurement of agglutination inhibition according to claim 2, wherein the ligand to be measured is human albumin, and the receptor is an anti-human albumin monoclonal antibody.

10. The method for measurement of agglutination inhibition according to claim 2, wherein an average particle diameter of the second insoluble carrier particle, which carries the receptor, is one half (½) to one tenth (¹⁄₁₀) an average particle diameter of the first insoluble carrier particle, which carries the ligand or ligand-like substance.

11. A reagent for agglutination-inhibition assay comprising the following:
   a first insoluble carrier particle that carries a plurality of a ligand or a plurality of a ligand-like substance,
   a first free-form receptor that binds specifically to a site on the ligand or the ligand-like substance, and
   a second insoluble carrier particle that carries a second receptor that is different from the first free-form receptor and binds specifically to a different site on the ligand or the ligand-like substance than the first free-form receptor,
   the assay being for measurement of an agglutination inhibition reaction of particles responsive to an amount of the ligand to be measured in a sample.

12. The reagent for agglutination-inhibition assay according to claim 11, wherein the first or second insoluble carrier particle is a latex particle.

13. The reagent for agglutination-inhibition assay according to claim 11, wherein the receptor is an antibody or a fragment including a functional site thereof, and the ligand is an antigen, the assay reagent being for measuring the agglutination inhibition reaction of the particles based on immunoreactions between the receptor and the ligand.

14. The reagent for agglutination-inhibition assay according to claim 11, wherein both the free-form receptor and the receptor which binds to a different site on the ligand than the free-form receptor are monoclonal antibodies.

15. The reagent for agglutination-inhibition assay according to claim 11, wherein the average particle diameter of the second insoluble carrier particle, which carries the receptor, is one half (½) to one tenth (¹⁄₁₀) the average particle diameter of the first insoluble carrier particle, which carries the ligand or ligand-like substance.

16. The reagent for agglutination-inhibition assay according to claim 11, wherein the ligand to be measured is human albumin, and the receptor is an anti-human albumin monoclonal antibody.

17. The reagent for agglutination-inhibition assay according to claim 12, wherein the receptor is an antibody or a fragment including a functional site thereof, and the ligand is an antigen, the assay reagent being for measuring the agglutination inhibition reaction of the particles based on immunoreactions between the receptor and the ligand.

18. The reagent for agglutination-inhibition assay according to claim 12, wherein both the free-form receptor and the receptor that binds to a different site on the ligand than the free-form receptor are monoclonal antibodies.

19. The reagent for agglutination-inhibition assay according to claim 12, wherein the average particle diameter of the second insoluble carrier particle, which carries the receptor, is one half (½) to one tenth (¹⁄₁₀) the average particle diameter of the first insoluble carrier particle, which carries the ligand or ligand-like substance.

20. The reagent for agglutination-inhibition assay according to claim 12, wherein the ligand to be measured is human albumin, and the receptor is an anti-human albumin monoclonal antibody.

* * * * *